United States Patent
Coe

Patent Number: 5,449,511
Date of Patent: Sep. 12, 1995

[54] NON-WHITENING ANTIPERSPIRANT COMPOSITION

[75] Inventor: Craig M. Coe, Sagamore, Mass.

[73] Assignee: The Gillette Company, Boston, Mass.

[21] Appl. No.: 90,368

[22] Filed: Jul. 12, 1993

Related U.S. Application Data

[63] Continuation of Ser. No. 764,918, Sep. 24, 1991, abandoned, which is a continuation-in-part of Ser. No. 569,947, Aug. 20, 1990, abandoned, which is a continuation-in-part of Ser. No. 408,124, Sep. 15, 1989, abandoned.

[51] Int. Cl.[6] .................. A61K 7/32; A61K 7/34; A61K 7/38
[52] U.S. Cl. .................. 424/66; 424/DIG. 5; 424/4.7; 424/68
[58] Field of Search .................. 424/65, 66, 67, 68, 424/DIG. 5

[56] References Cited

U.S. PATENT DOCUMENTS

| | | | |
|---|---|---|---|
| 4,280,994 | 7/1981 | Turney | 424/68 |
| 4,425,328 | 1/1984 | Nabial | 424/68 |
| 4,511,554 | 4/1985 | Geria | 424/65 |
| 4,524,062 | 6/1985 | Laba | 424/65 |
| 4,673,570 | 6/1987 | Soldati | 424/66 |
| 4,704,271 | 11/1987 | Hourihan | 424/66 |
| 4,719,103 | 1/1988 | Krevald | 424/66 |
| 4,720,381 | 1/1988 | Schamper | 424/66 |
| 4,722,836 | 2/1988 | Geary | 424/68 |
| 4,725,432 | 2/1988 | May | 424/066 |
| 4,743,444 | 5/1988 | McCall | 424/65 |
| 4,775,528 | 10/1988 | Callaghan | 424/66 |
| 4,781,917 | 11/1988 | Luebbe | 424/65 |
| 4,832,945 | 5/1989 | Osipow et al. | 424/68 |
| 4,840,789 | 6/1989 | Orr et al. | 424/68 |
| 4,853,214 | 8/1989 | Orr | 424/68 |
| 4,985,238 | 1/1991 | Tanner | 424/68 |
| 5,019,375 | 5/1991 | Tanner et al. | 424/66 |

FOREIGN PATENT DOCUMENTS

| | | | |
|---|---|---|---|
| 120210 | 10/1984 | European Pat. Off. | 424/68 |
| 400546 | 12/1990 | European Pat. Off. | 424/66 |
| 404532 | 12/1990 | European Pat. Off. | 424/68 |
| 424282 | 4/1991 | European Pat. Off. | A61K 7/00 |
| 2242969 | 4/1975 | France | 424/68 |
| 89 185978/26 | 6/1989 | France | A61K 7/42 |
| 87-307865/44 | 11/1987 | WIPO | A61K 7/00 |

OTHER PUBLICATIONS

Technical Bulletin MACOL 57, PPG Mazer, Sep. 1989 (or earlier), No Date Thereon.

*Primary Examiner*—Dale R. Ore
*Attorney, Agent, or Firm*—Stephan P. Williams

[57] ABSTRACT

An anhydrous antiperspirant product includes an anhydrous carrier vehicle; an antiperspirant active salt suspended in particle form in the vehicle; and a nonvolatile water soluble liquid masking agent that is interactive with the antiperspirant active salt to essentially eliminate discernible whitening without substantially inhibiting the antiperspirant activity of the salt when the product is applied to the skin.

7 Claims, No Drawings

NON-WHITENING ANTIPERSPIRANT COMPOSITION

This application is a continuation of Ser. No. 07/764,918 filed Sep. 24, 1991, now abandoned, which is a continuation-in-part of Ser. No. 07/569,947 filed Aug. 20, 1990, now abandoned, which is a continuation-in-part of Ser. No. 07/408,124 filed Sep. 15, 1989, now abandoned.

This invention relates to antiperspirant products.

Antiperspirant products are well-known in the cosmetic art. One class of such products contains a suspension of an active antiperspirant ingredient, e.g., aluminum chlorohydrate, in particulate form. The antiperspirant active ingredient acts to prevent perspiration, it is believed, by going into solution in the presence of body moisture, and interacting with the sweat glands. Solid-type antiperspirants of this type typically include a gelling agent (gellant) that gives the product a solid character. These are applied by rubbing an area of the body with product to apply a layer to the skin. It is desirable that the solid product glide smoothly without flaking or crumbling. Application of antiperspirant products frequently result in objectionable aesthetic characteristics such as tackiness, and whitening, i.e., the presence of visible residues of white appearance on the skin.

Many of the desirable properties of antiperspirants can be achieved by including various ingredients to the product formulation in addition to the active agent, the vehicle and, in solids, the gelling agent. For example, surfactants may be added to ease washing of the product from the skin after use; fragrance and preservatives are commonly added; and supplemental emollients may be added to improve the application characteristics, glide, flaking, crumbling (in solids), etc. However, such additives tend to reduce the efficacy of the product. It is believed, for example, that emollients tend to encapsulate or enrobe particulates of the active ingredient and retard the dissolution and, therefore interfere with the interaction of the active antiperspirant ingredient with the sweat glands.

In accordance with one aspect of the invention, there is provided a nonaqueous antiperspirant product that includes a nonaqueous carrier vehicle; an antiperspirant active salt suspended in particle form in the carrier vehicle; and a nonvolatile, water-soluble, liquid (at 25° C.) masking agent that interacts with the antiperspirant active to essentially eliminate discernible whitening without substantially inhibiting the antiperspirant activity of the salt when the product is applied to the skin. The masking agent in preferred embodiments is a nonvolatile aliphatic compound (such as alcohols, ethers, silanols, silyl ethers, siloxanes and silicones) which contains disubstituted oxygen functionalities, for example, alkoxylated alcohols. The masking agent in particular embodiments has an alkoxylated alcohol functionality with a butane backbone, for example PPG-10 Butanediol, or a polysiloxane backbone, for example dimethicone copolyol. As used herein, the term "nonvolatile" means that the masking agent has a boiling point of at least about 150° C.; and the term "water soluble" means that the masking agent is soluble at a level of at least about five percent in water.

Preferred antiperspirant products include a sufficient quantity of a gelling agent so that the antiperspirant product can be used as a solid, but a reduced amount of, or no, gelling agent may be used if it is desirable to make a more liquid type product.

The vehicle generally is volatile and preferably makes up between about thirty to about fifty percent of the product and in preferred embodiments, is a volatile silicone such as cylcomethicone. Other suitable vehicles include aliphatic hydrocarbons such as isododecane, dimethicone, polyphenylmethylsiloxane liquids such as Dow Corning DC-556, and $C_{12-15}$ Alcohols Benzoate (Finsolv TN).

The active ingredient, in particulate form, is suspended in the carrier vehicle. Preferred active antiperspirant active components for use in the antiperspirant products include well-known salts such as aluminum zirconium chlorohydrates, aluminum chlorohydrates and other polyhydroxy complexes of basic aluminum salts, such as aluminum sesquichlorohydrate, aluminum dichlorohydrate, aluminum chloride, aluminum zirconium trichlorohydrate, aluminum zirconium tetrachlorohydrate, aluminum zirconium pentachlorohydrate and aluminum zirconium octachlorohydrate. A particularly preferred active ingredient is Aluminum Zirconium Tetrachlorohydrex-Gly with enhanced activity (as described in U.S. Pat. No. 4,775,528). The active antiperspirant component(s) should be present in an amount effective to reduce perspiration when applied to the skin. The precise limits on the amount of active antiperspirant component that can be used will vary with the particular component and formula. As a general rule, however, the antiperspirant product should contain anywhere from about ten to about thirty percent (more preferably about twenty-five percent) of active antiperspirant component. The active ingredient is provided in particulate form, for ease of processing and to avoid settling from the suspension. In preferred embodiments, the products of the invention do not require conventional suspending agents such as clays and silicas (e.g., bentonite). Preferably at least fifty percent of the particulates of the antiperspirant active are of about ten microns or less in size, and more preferably at least ninety percent of the particulates of the antiperspirant active are of about ten microns or less in size (Superfine). Larger particulates may also be used.

The masking agent, in quantity less than fifty percent by weight, preferably about twenty to forty percent by weight, of the antiperspirant active salt, and two to nine percent by weight of the total product provides essentially complete absence of discernible whitening, without substantial inhibition of antiperspirant activity. The masking agent preferably is a water soluble liquid nonvolatile emollient material (i.e., it enhances glide and smoothness of application) and, it is believed, reduces whitening by interacting with the particulates to produce an optical effect that tends to reduce light scattering and apparent whiteness. The agent does not, however, substantially impede dissolution of the antiperspirant ingredient by body fluids or the interaction of the dissolved antiperspirant ingredient with the sweat glands. Preferred masking agents include PPG-10 Butanediol (MACOL 57) (Mazer Chemicals, Gurnee, Ill.) and dimethicone copolyols (Dow Corning 190 and 193 surfactants).

In addition, for solids, gelling agents may be included. Examples of suitable gelling agents include hydrogenated castor oil, fatty alcohols such as stearyl alcohol, Stearamide MEA, polyethylene-vinyl acetate copolymers, polyethylene homopolymers and blends and combinations of these. Preferably, the amount of gelling agent in the solid antiperspirant product should be sufficient to cause the liquid vehicle to gel (i.e., become free-standing). In general, the solid antiperspirant product should include between about fifteen percent and about twenty-five percent (more preferably about twenty percent) of gelling agent. For liquid antiperspirant products, it may be desirable to use some gelling agent in the antiperspirant product for thickening, even though a sufficient quantity of gelling agent is not used to obtain a free-standing composition.

Other compatible emollients, surfactants, preservatives, fragrances and additionally supplemental emollients generally range from about one to about ten percent of the product and may be dioctyl cyclohexane, propoxylated ethers such as PPG-14 Butyl Ether, isopropyl palmitate, isopropyl myristate, myristal myristate, dimethicone, $C_{12-15}$ Alcohol Benzoates, diisopropyl sebacate, and diisopropyl adipate. These can add to desirable aesthetic properties such as smoothness, glide, and the perception of drier and nontacky application.

In one particular embodiment, the product is a solid antiperspirant including a volatile cyclomethicone (DC-345) carrier, Superfine Aluminum-Zirconium Tetrachlorohydrex-Gly active ingredient of enhanced activity (as in U.S. Pat. No. 4,775,528), a PPG-10 Butanediol (MACOL 57) water soluble masking agent, myristyl myristate emollient, PEG-8 Distearate surfactant, and hydrogenated castor oil and stearyl alcohol gelling agents. The ingredients are formulated in concentrations for balanced stability, aesthetics and efficacy. In particular embodiments, the gelling agents may range from fifteen to twenty-five percent and supplemental emollients may range from one to ten percent. Active ingredient particles of less than ten microns size are in a solid suspension within a matrix formed substantially of the gelling agent. The final product is a free standing solid suspension of active antiperspirant ingredient particles. In a particular embodiment, the solid antiperspirant product includes forty-three to forty-six percent by weight carrier vehicle, twenty-one to twenty four percent by weight antiperspirant active ingredient, seventeen to twenty percent by weight gelling agent, five to seven percent by weight supplemental nonaqueous emollient material; and four to six percent by weight nonvolatile, water-soluble, liquid masking agent.

The following Examples illustrate representative antiperspirant products and are given by way of illustration only and are not to be considered as being limiting. The amounts in the Examples and the claims are in weight percent. The formulations of the Examples provide antiperspirant products that are characterized by essentially complete absence of discernable (to an experienced visual evaluator) whitening and provide antiperspirant efficacy (as measured clinically by gravimetric means) that is not substantially impaired by the masking agent, that is the antiperspirant efficacy of a product with a masking agent in accordance with the invention is substantially the same as the antiperspirant efficacy of a product of the same formulation in which the masking agent is omitted and the vehicle quantity is increased in compensation for the omission of the masking agent. The solid products also exhibit smooth glide upon application without flaking or crumbling. The ingredients may be processed as described or conventionally known. For roll-on or aerosol products, the ingredients, following teachings herein, may be processed as conventionally known.

| CTFA NAME | % Active |
| --- | --- |
| CYCLOMETHICONE (DC-345) | 44.6 |
| ALUMINUM ZIRCONIUM TETRACHLOROHYDREX-GLY | 22.7 |
| STEARYL ALCOHOL | 15.6 |
| PPG-10 BUTANEDIOL (MACOL 57) | 4.8 |
| C12-15/ALCOHOLS BENZOATE (FINSOLV TN) | 3.8 |
| HYDROGENATED CASTOR OIL | 2.8 |
| FRAGRANCE/STARCH/POLYOL | 2.4 |
| MYRISTYL MYRISTATE | 1.9 |
| PEG-8 DISTEARATE | 0.9 |
| FRAGRANCE | 0.5 |
| | 100.0 |

The Example 1 solid product is made by combining and mechanically mixing the vehicle, the masking agent and supplemental emollients until homogeneous. The active ingredient in powder form is then added, and the mixture is heated from room temperature to 60° C. over a period of about one-quarter hour. At 60° C., gellant (i e , hydrogenated castor oil and stearyl alcohol) is added and the mixture is continued to be heated to about 85° C. (a temperature where the gellant has melted) with agitation to insure complete homogeneity. The mixture is cooled to about 64° C. and fragrance is added. The mixture is further cooled to about 53° C. and poured into suitable containers. The product of this Example 1 has antiperspirant efficacy that is unsurpassed by commercially available solid antiperspirant products as measured clinically in a hot room by gravimetric sweat reduction determinations.

| CTFA NAME | % ACTIVE |
| --- | --- |
| CYCLOMETHICONE (DC-345) | 48.1 |
| ALUMINUM ZIRCONIUM TETRACHLOROHYDREX-GLY | 22.7 |
| STEARYL ALCOHOL | 15.5 |
| DIMETHICONE COPOLYOL (DOW CORNING 190 SURFACTANT) | 5.0 |
| HYDROGENATED CASTOR OIL MP 70 | 2.8 |
| FRAGRANCE/STARCH/POLYOL | 2.4 |
| MYRISTYL MYRISTATE | 2.0 |
| PEG-8 DISTEARATE | 0.9 |
| FRAGRANCE | 0.6 |
| | 100.0 |

The ingredients of Example 2 are processed using a procedure similar to Example 1 with the mixture being heated to about 95° C. after addition of the gellant, the temperature being held for about fifteen minutes, then cooled to 80°–85° C., and after fragrance is added, the mixture is stirred and immediately poured into suitable containers.

EXAMPLE 3

| CTFA NAME | % ACTIVE |
| --- | --- |
| CYCLOMETHICONE (DC-345) | 48.3 |
| ALUMINUM ZIRCONIUM TETRACHLOROHYDREX-GLY | 23.6 |
| STEARYL ALCOHOL | 15.2 |
| PPG-10 BUTANEDIOL (MACOL 57) | 5.0 |
| HYDROGENATED CASTOR OIL MP 70 | 2.9 |
| TALC | 2.2 |
| STEARETH-21 (Brij 721S) | 1.0 |
| PEG-8 DISTEARATE | 1.0 |
| FRAGRANCE | 0.6 |
| PROPYLPARABEN | 0.2 |

| CTFA NAME | % ACTIVE |
| --- | --- |
| | 100.0 |

The Example 3 solid product is made by combining and mechanically mixing the vehicle, the masking agent and supplemental emollients until homogeneous. The active ingredient in powder form is then added, and the mixture is heated from room temperature to 60° C. over a period of about one-quarter hour. At 60° C., gellant is added and the mixture is continued to be heated to about 85° C. (a temperature where the gellant has melted) with agitation to insure complete homogeneity. The mixture is cooled to about 64° C. and fragrance is added. The mixture is further cooled to about 53° C. and poured into suitable containers.

EXAMPLE 4

| CTFA NAME | % ACTIVE |
| --- | --- |
| CYCLOMETHICONE (DC-345) | 47.7 |
| ALUMINUM ZIRCONIUM TETRACHLORO-HYDREX-GLY | 23.3 |
| STEARYL ALCOHOL | 15.0 |
| PPG-10 BUTANEDIOL (MACOL 57) | 5.0 |
| HYDROGENATED POLYISOBUTENES (Panalane) | 2.0 |
| HYDROGENATED CASTOR OIL MP 70 | 3.0 |
| TALC | 1.2 |
| STEARETH-21 (Brij 721S) | 1.0 |
| PEG-8 DISTEARATE | 1.0 |
| FRAGRANCE | 0.6 |
| PROPYLPARABEN | 0.2 |
| | 100.0 |

The Example 4 solid product is made by combining and mechanically mixing the vehicle, the masking agent and supplemental emollients until homogeneous. The active ingredient in powder form is then added, and the mixture is heated from room temperature to 60° C. over a period of about one-quarter hour. At 60° C., gellant is added and the mixture is continued to be heated to about 85° C. (a temperature where the gellant has melted) with agitation to insure complete homogeneity. The mixture is cooled to about 64° C. and fragrance is added. The mixture is further cooled to about 53° C. and poured into suitable containers.

EXAMPLE 5

| CTFA NAME | % ACTIVE |
| --- | --- |
| CYCLOMETHICONE (DC-345) | 45.9 |
| ALUMINUM ZIRCONIUM TETRACHLORO-HYDREX-GLY | 22.7 |
| STEARYL ALCOHOL | 15.5 |
| PPG-10 BUTANEDIOL (MACOL 57) | 4.8 |
| HYDROGENATED POLYISOBUTENES (PANALANE) | 3.8 |
| HYDROGENATED CASTOR OIL MP 70 | 2.8 |
| MYRISTYL MYRISTATE | 2.0 |
| STEARETH-21 (Brij 721S) | 1.0 |
| PEG-8 DISTEARATE | 0.9 |
| FRAGRANCE | 0.6 |
| | 100.0 |

The Example 5 solid product is made by combining and mechanically mixing the vehicle, the masking agent and supplemental emollients until homogeneous. The active ingredient in powder form is then added, and the mixture is heated from room temperature to 60° C. over a period of about one-quarter hour. At 60° C., gellant is added and the mixture is continued to be heated to about 85° C. (a temperature where the gellant has melted) with agitation to insure complete homogeneity. The mixture is cooled to about 64° C. and fragrance is added. The mixture is further cooled to about 53° C. and poured into suitable containers. The product of this Example 5 has antiperspirant efficacy that is unsurpassed by commercially available solid antiperspirant products as measured clinically in a hot room by gravimetric sweat reduction determinations.

| CTFA NAME | % ACTIVE |
| --- | --- |
| CYCLOMETHICONE (DC-345) | 45.4 |
| ALUMINUM ZIRCONIUM TETRACHLORO-HYDREX-GLY | 22.7 |
| STEARYL ALCOHOL | 15.5 |
| PPG-10 BUTANEDIOL (MACOL 57) | 4.8 |
| HYDROGENATED CASTOR OIL MP 70 | 2.8 |
| FRAGRANCE/STARCH/POLYOL | 2.4 |
| DIMETHICONE COPOLYOL (DOW CORNING 190 SURFACTANT) | 2.0 |
| MYRISTYL MYRISTATE | 2.0 |
| PEG-8 DISTEARATE | 0.9 |
| FRAGRANCE | 0.5 |
| | 100.0 |

EXAMPLE 7

| CTFA NAME | % ACTIVE |
| --- | --- |
| CYCLOMETHICONE (DC-345) | 45.5 |
| ALUMINUM ZIRCONIUM TETRACHLORO-HYDREX-GLY | 22.7 |
| STEARYL ALCOHOL | 15.5 |
| PPG-10 BUTANEDIOL (MACOL 57) | 4.8 |
| HYDROGENATED CASTOR OIL MP 70 | 2.8 |
| FRAGRANCE/STARCH/POLYOL | 2.4 |
| DIMETHICONE COPOLYOL (DOW CORNING 193 SURFACTANT) | 2.0 |
| MYRISTYL MYRISTATE | 1.9 |
| PEG-8 DISTEARATE | 0.9 |
| FRAGRANCE | 0.5 |
| | 100.0 |

EXAMPLE 8

| CTFA NAME | % ACTIVE |
| --- | --- |
| CYCLOMETHICONE (DC-345) | 48.3 |
| ALUMINUM ZIRCONIUM TETRACHLORO-HYDREX-GLY | 22.7 |
| STEARYL ALCOHOL | 15.5 |
| DIMETHICONE COPOLYOL (DOW CORNING 193 SURFACTANT) | 5.0 |
| HYDROGENATED CASTOR OIL MP 70 | 2.8 |
| FRAGRANCE/STARCH/POLYOL | 2.4 |
| MYRISTYL MYRISTATE | 1.9 |
| PEG-8 DISTEARATE | 0.9 |
| FRAGRANCE | 0.5 |
| | 100.0 |

The ingredients of Examples 6–8 are processed using a procedure similar to Example 5 with the mixture being heated to about 95° C. after addition of the gellant, the temperature being held for about fifteen minutes, then cooled to 80°–85° C., and after fragrance is added, the mixture is stirred and immediately poured into suitable containers.

While particular embodiments of the invention have been shown and described, various modifications will be apparent to those skilled in the art, and therefore it is not intended that the invention be limited to the disclosed embodiments or to details thereof, and departures may be made therefrom within the spirit and scope of the invention.

What is claimed is:

1. A non-aqueous solid antiperspirant composition comprising:
   about thirty to fifty percent by weight of a non-aqueous carrier vehicle;
   about ten to thirty percent by weight of an antiperspirant active ingredient suspended in particulate form in said vehicle;
   about fifteen to twenty-five percent by weight of a gelling agent; and
   about two to nine percent by weight of a non-volatile, water-soluble dimethicone copolyol liquid masking agent.

2. The composition of claim 1 wherein said carrier vehicle is selected from the group consisting of cyclomethicone, aliphatic hydrocarbons, dimethicone, polyphenylmethylsiloxane liquids, and $C_{12-15}$ Alcohols Benzoate;
   said antiperspirant active ingredient is selected from the group consisting of aluminum zirconium chlorohydrate, aluminum chlorohydrate, and polyhydroxy complexes of basic aluminum salts; and
   said gelling agent is selected from the group consisting of hydrogenated castor oil, fatty alcohols, Stearamide MEA, polyethylene vinyl acetate copolymers, polyethylene homopolymers, and mixtures thereof.

3. The composition of claim 2 further comprising about one to ten percent by weight of an emollient selected from the group consisting of propoxylated ethers, dioctyl cyclohexane, isopropyl palmitate, isopropyl myristate, myristyl myristate, dimethicone, $C_{12-15}$ Alcohol Benzoates, diisopropyl sebacate, diisopropyl adipate, and mixtures thereof.

4. The composition of claim 3 wherein at least ninety percent of said active ingredient comprises particles of about ten microns or less in size.

5. The composition of claim 2 wherein said carrier vehicle is cyclomethicone.

6. The composition of claim 5 comprising about forty-three to forty-six percent by weight of said carrier vehicle, about twenty-one to twenty-four percent by weight of said antiperspirant active ingredient, at least ninety percent of said antiperspirant active ingredient comprising particles of about ten microns or less in size, about seventeen to twenty percent by weight of said gelling agent and about four to six percent by weight of said masking agent.

7. The composition of claim 6 further comprising about five to seven percent of an emollient.

* * * * *

UNITED STATES PATENT AND TRADEMARK OFFICE
CERTIFICATE OF CORRECTION

PATENT NO. : 5,449,511
DATED : September 12, 1995
INVENTOR(S) : Craig M. Coe and Nancy M. Karassik It is certified that error appears in the above-indentified patent and that said Letters Patent is hereby corrected as shown below:

On the title page, add as an Inventor -- Nancy M. Karassik, Concord, Mass. --.

Signed and Sealed this

Fifth Day of December, 1995

Attest:

BRUCE LEHMAN

Attesting Officer

Commissioner of Patents and Trademarks